US009486193B2

United States Patent
Vidlund et al.

(10) Patent No.: US 9,486,193 B2
(45) Date of Patent: Nov. 8, 2016

(54) PROCEDURAL SHEATH SECUREMENT DEVICE AND METHODS

(71) Applicant: St. Jude Medical Puerto Rico LLC, Caguas, PR (US)

(72) Inventors: Robert M. Vidlund, Forest Lake, MI (US); Zachary J. Tegels, Minneapolis, MN (US); Martha Escobar, Jordan, MN (US); Russell D. Terwey, St. Michael, MN (US); Douglas P. Killion, Maple Grove, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 372 days.

(21) Appl. No.: 13/744,218

(22) Filed: Jan. 17, 2013

(65) Prior Publication Data

US 2013/0190809 A1 Jul. 25, 2013

Related U.S. Application Data

(60) Provisional application No. 61/590,065, filed on Jan. 24, 2012.

(51) Int. Cl.
*A61B 17/08* (2006.01)
*A61F 11/00* (2006.01)
*A61B 17/00* (2006.01)
*A61B 17/34* (2006.01)

(52) U.S. Cl.
CPC ........ *A61B 17/0057* (2013.01); *A61B 17/3415* (2013.01); *A61B 90/11* (2016.02); *A61B 2017/00654* (2013.01); *A61B 2017/347* (2013.01); *A61B 2017/3407* (2013.01)

(58) Field of Classification Search
CPC ........... A61M 25/02; A61B 17/00491; A61B 17/0057; A61B 17/12022; A61B 17/3415; A61B 2017/00646; A61B 2017/00623; A61B 2017/00637
See application file for complete search history.

(56) References Cited

U.S. PATENT DOCUMENTS

| 4,593,681 | A | * | 6/1986 | Soni ............................ 600/102 |
| 5,201,742 | A | * | 4/1993 | Hasson ................ A61B 19/201 606/1 |
| 5,263,956 | A | | 11/1993 | Nobles |
| 5,437,645 | A | * | 8/1995 | Urban .................... A61B 17/34 604/165.02 |

(Continued)

FOREIGN PATENT DOCUMENTS

| WO | 03001969 A2 | 1/2003 |
| WO | 2006081409 A2 | 8/2006 |

(Continued)

OTHER PUBLICATIONS

Notification of Transmittal of the International Search Report and the Written Opinion of the International Searching Authority, or the Declaration for PCT International No. PCT/US2013/021813, mailed Apr. 2, 2013 (15 pp.).

*Primary Examiner* — Tuan V Nguyen
(74) *Attorney, Agent, or Firm* — Holland & Hart

(57) ABSTRACT

A procedural sheath holding device includes a base member and a securing member. The base member is positionable in contact with an outer skin surface adjacent to an incision. The securing member is attached to the base member and includes a securing portion operable to releasably secure a procedural sheath in a fixed axial position relative to the skin surface when a vascular closure device is inserted through the procedural sheath to seal the incision. The securing member may be pivotal relative to the base member.

12 Claims, 13 Drawing Sheets

(56) References Cited

U.S. PATENT DOCUMENTS 5,658,272 A     8/1997   Hasson
6,071,300 A *   6/2000   Brenneman et al. ......... 606/213

FOREIGN PATENT DOCUMENTS

| WO | 2007084588 A2 | 7/2007 |
| WO | 2010017641 A1 | 2/2010 |

* cited by examiner

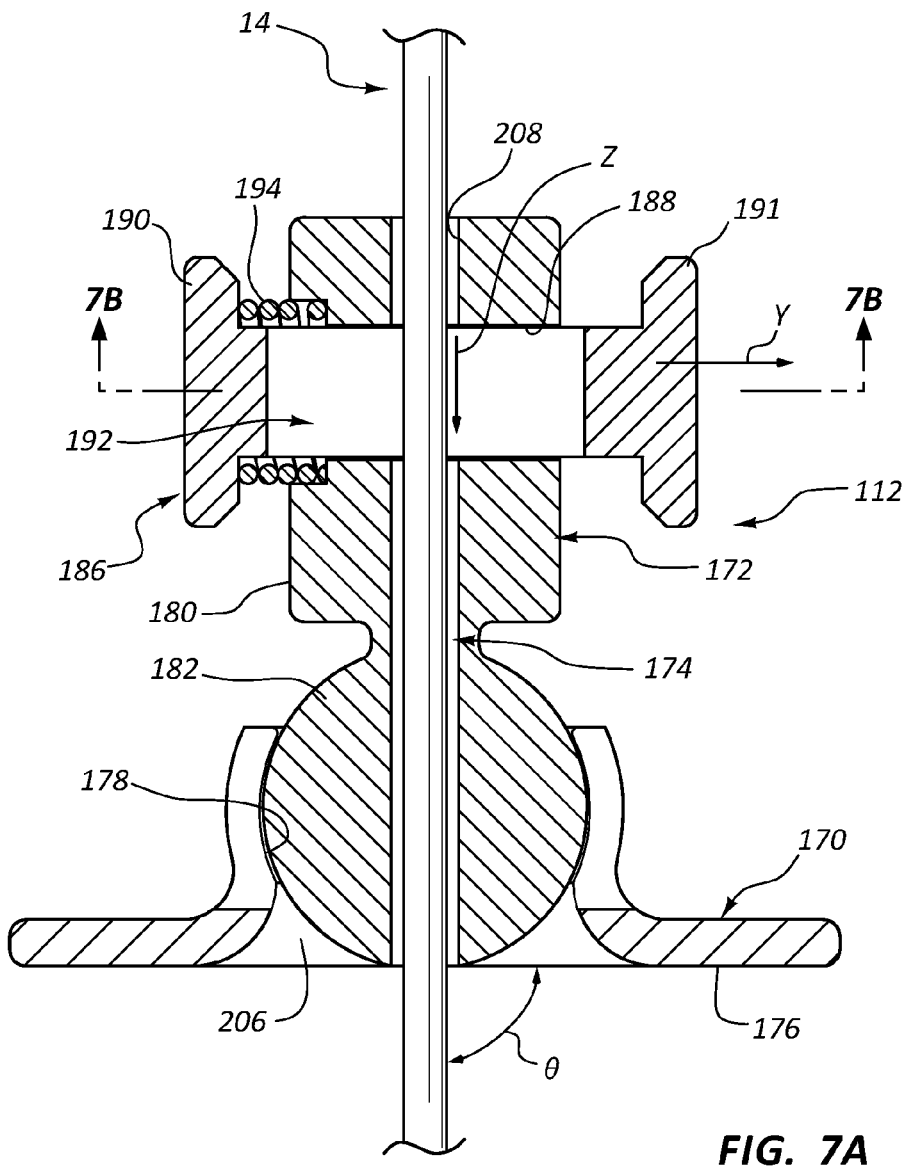
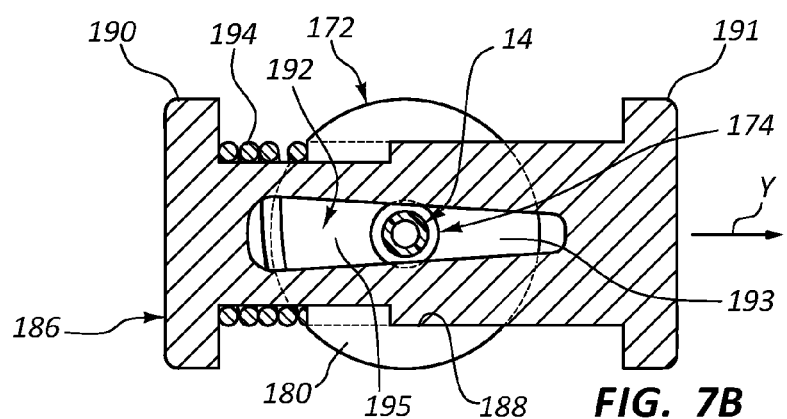
FIG. 7A
FIG. 7B

PROCEDURAL SHEATH SECUREMENT DEVICE AND METHODS

CROSS-REFERENCE TO RELATED APPLICATION

This application claims the benefit of the filing date of U.S. Provisional Application No. 61/590,065, filed Jan. 24, 2012, and entitled PROCEDURAL SHEATH SECUREMENT DEVICE AND METHODS, the disclosure of which is incorporated, in its entirety, by this reference.

TECHNICAL FIELD

The present disclosure relates generally to systems and methods for treating tissue punctures, and more particularly, to devices and methods for supporting procedural sheaths during treatment of tissue punctures.

BACKGROUND

Various surgical procedures are routinely carried out intravascularly or intraluminally. For example, in the treatment of vascular disease, such as arteriosclerosis, it is a common practice to access the artery and insert an instrument (e.g., a balloon or other type of catheter) to carry out a procedure within the artery. Such procedures usually involve the percutaneous puncture of the artery so that an insertion sheath may be placed in the artery and thereafter instruments (e.g., catheters) may pass through the sheath to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices.

While there are a variety of prior art devices and techniques for closing such punctures, one primary challenge involves locating the vessel puncture subcutaneously and determining with some accuracy the location of portions of the closure device relative to the vessel puncture.

SUMMARY

One aspect of the present disclosure relates to a procedural sheath holding device that includes a base member and a securing member. The base member is positionable in contact with an outer skin surface adjacent to an incision. The securing member is pivotally attached to the base member and includes a securing portion operable to releasably secure a procedural sheath in a fixed axial position relative to the skin surface when a vascular closure device is inserted through the procedural sheath to seal the incision.

The procedural sheath holding device may include a passage extending through the base member and securing member that is sized to receive the procedural sheath. The securing member may be configured to contact the procedural sheath within the passage. The securing member may be operable laterally to capture the procedural sheath against a fixed wall within the passage. The securing member may be operable to apply a radial compression force on the procedural sheath.

Another aspect of the present disclosure relates to a procedural sheath holding member that includes a base member, a pivot member, a passage, and a securing device. The base member includes a first end in contact with a skin surface adjacent to a tissue puncture. The pivot member is pivotally attached to the base member and spaced from the skin surface by the base member. The passage extends through the base member and pivot member and is configured for passage of a procedural sheath therethrough. The securing device is operable within the passage to fix an axial position of the procedural sheath relative to the skin surface.

The securing device may be positioned on the pivot member. The securing device may be operable to apply a lateral force to the procedural sheath within the passage. The securing device may include a securement portion (also referred to as a slider) having a slot through which the procedural sheath passes, wherein actuating the securement portion captures the procedural sheath between a surface of the pivot member and a surface of the securement portion. The securing device may be operable to apply a radially constricting force on the procedural sheath. The base member may include a socket feature and the pivot member includes a ball member that interfaces with the socket feature.

Another aspect of the present disclosure relates to a method of securing a position of a first portion of a vascular closure assembly positioned in a tissue puncture. The method includes providing a securing device that includes a tissue surface interface, a passage, and a securing member, positioning the tissue surface interface in contact with a skin surface adjacent to the tissue puncture, inserting the first portion of the vascular closure assembly through the passage and into the tissue puncture, and operating the securing member to fix an axial position of the first portion of the vascular closure assembly relative to the skin surface.

The method may also include pivoting a portion of the securing device to change an angled orientation of the first portion of the vascular closure assembly relative to the skin surface. The method may include performing a procedure with a second portion of the vascular closure assembly subcutaneously while the axial position of the first portion of the vascular closure assembly is fixed with the securing member. The method may include applying a radially constrictive force to the first portion of the vascular closure assembly with the securing member. The method may include applying a lateral force to the first portion of the closure assembly with the securing member. The first portion of the vascular closure assembly may include a procedural sheath.

Another method in accordance with the present disclosure relates to sealing closed a vascular puncture accessible through a percutaneous incision. The method includes providing a vascular closure assembly and a skin securement device, wherein the vascular closure assembly includes a procedural sheath and a vascular closure device. The method includes mounting the skin securement device to the procedural sheath, inserting the procedural sheath through the percutaneous incision and vascular puncture, inserting the vascular closure device through the procedural sheath to the vascular puncture, and conducting a first operation of the vascular closure device. The method also includes contacting the skin securement device against a skin surface adjacent to the percutaneous incision, operating the skin securement device to fix an axial position of the procedural sheath relative to the skin surface, and conducting a second operation of the vascular closure device to seal the vascular puncture.

The first operation of the vascular closure device may include inflating a balloon, anchoring the balloon against an inner surface of a vessel adjacent to the vascular puncture, and delivering a bioadhesive sealant to the vascular puncture. The second operation of the vascular closure device may include withdrawing the vascular closure device from the vascular puncture and depositing a sealing tip within the bioadhesive sealant. The skin securement device may include a base portion and a securing portion. The base portion may be arranged to contact the skin surface, and the method may include pivotally adjusting the securing portion relative to the base portion to alter an insertion angle of the procedural sheath into the percutaneous incision. The skin securement device may include a securing member, and fixing an axial position of the procedural sheath relative to the skin surface may include applying a lateral force to the procedural sheath with the securing member. The skin securement device may include a securing member, and fixing an axial position of the procedural sheath relative to the skin surface may include applying a radially constrictive force to the procedural sheath with the securing member.

The foregoing and other features, utilities, and advantages of the invention will be apparent from the following detailed description of the invention with reference to the accompanying drawings.

BRIEF DESCRIPTION OF THE DRAWINGS

The accompanying drawings illustrate various embodiments of the present disclosure and are a part of the specification. The illustrated embodiments are merely examples of the present disclosure and do not limit the scope attic invention.

FIG. 7A is a cross-sectional view of the skin securement device of FIG. 6A in an actuated position.

FIG. 7B is a cross-sectional view of the skin securement device of FIG. 7A taken along cross-section indicators 7B-7B.

Throughout the drawings, identical reference numbers designate similar, but not necessarily identical, elements.

DETAILED DESCRIPTION

Figure 1:
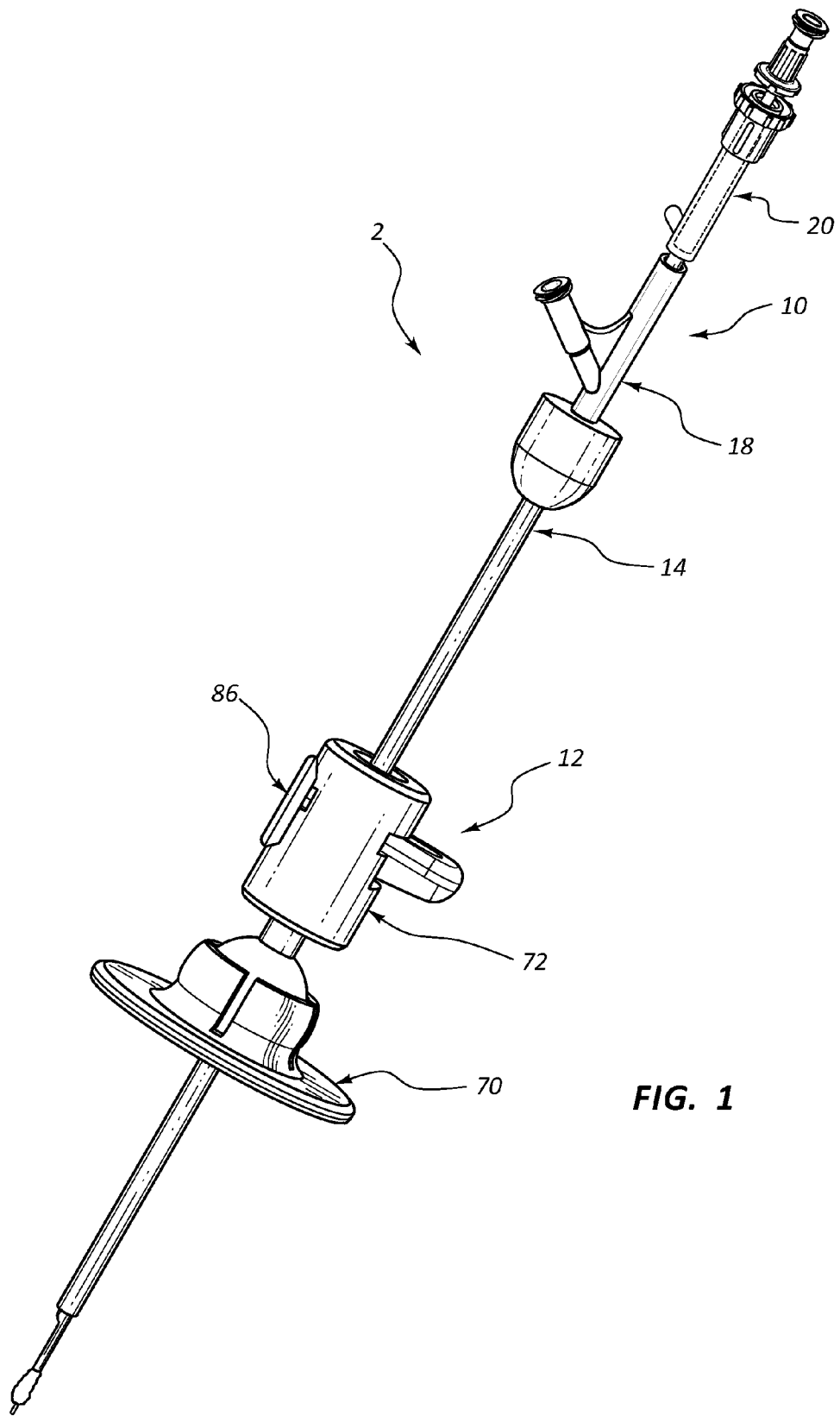
FIG. 1 is a perspective view of an assembly that includes a vascular closure assembly and a skin securement device in accordance with the present disclosure.

The systems disclosed herein may be used to close or seal percutaneous punctures made through the body tissue of a patient to gain access to a body cavity of a patient. Access through these percutaneous punctures allows a physician to carry out various procedures in or through the body cavity for examination, surgery, treatment and the like. While not meant to be limiting, the systems are illustrated being used to seal percutaneous punctures that provide access to blood vessels in patients for various procedures. It will be appreciated that the systems are applicable to other procedures requiring sealing of a puncture through body tissue into a cavity including, for example, laparoscopic surgery and other microscopic surgery techniques using a relatively small incision.

As used in the specification and the appended claims, the terms "engage" and "engagable" are used broadly to mean interlock, mesh, or contact between two structures or devices. Likewise "disengage" or "disengagable" means to remove or capable of being removed from interlock, mesh, or contact. A "tube" is an elongated device with a passageway. The passageway may be enclosed or open (e.g., a trough). A "lumen" may refer to any open space or cavity, including a cavity in a bodily organ, and especially in a blood vessel. The words "including" and "having," as well as their derivatives, as used in the specification, including the claims, have the same meaning as the word "comprising."

The general structure and function of tissue closure devices used for sealing a tissue puncture in an internal tissue wall accessible through an incision in the skin are well known in the art. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

An exemplary embodiment of the present disclosure relates to a vascular closure system that includes a procedural sheath, a vascular closure device, and a skin securement device. The procedural sheath provides access to a vessel puncture through a tissue tract. The vascular closure device is advanced through the procedural sheath to the vascular puncture. The vascular closure device delivers a sealant to the vascular puncture to seal the vascular puncture. The skin securement device may be used to fix an axial position of the sheath relative to an outer skin surface of the patient. The axially fixed procedural sheath may provide a reference point for positioning the vascular closure device relative to the vascular puncture. In at least one arrangement, the skin securement device retains the procedure sheath in a fixed axial position while moving the vascular closure device into a position where a sealing tip or secondary sealing material is deposited outside of the blood vessel and adjacent to the vascular puncture.

The skin securement device may include a base member, a securement portion, and a sheath passage. The sheath passage may extend through both the base member and the securement portion. The base member may include a skin contact surface that provides an interface between the skin securement device and an outer skin surface of the patient adjacent to a percutaneous incision that leads to the vessel puncture. The base member and securement portion may be connected together with a ball-and-socket connection that provides relative pivotal motion to assist in orienting the procedural sheath and vascular closure device at various angles relative to the tissue puncture.

The securement portion of the skin securement device may include various securing, constricting or other connecting features that operate to fix a position of the procedural sheath within the sheath passage, thereby fixing an axial position of the procedural sheath in at least one direction relative to the skin surface of the patient.

In one example, the vascular closure device is operable to temporarily seal the vascular puncture from within the vessel using an inflatable or expandable structure such as a balloon. The vascular closure device is operated to deliver a first volume of bioadhesive sealant to an exterior of the vessel to seal the vessel puncture. Prior to deflating the balloon, the skin securement device is positioned in contact with the outer skin surface of the patient and operated to fix an axial position of the procedural sheath relative to the skin securement device. Thereafter, the balloon is deflated and the vascular closure device is retracted out of the vessel and into a position wherein a distal end of the vascular closure device is positioned outside of and adjacent to the vascular puncture. The procedural sheath maintains a fixed axial position using the skin securement device.

The vascular closure device may be operated to deliver or dispose a second sealant within the first sealant in one example, the second sealant is a flow of secondary bioadhesive material. In another arrangement, the second sealant is a detachable sealing tip that comprises, for example, collagen. By fixing the axial position of the procedural sheath relative to the skin surface prior to withdrawing the vascular closure device, the operator, knowing the dimensions of the vascular closure device and depth of the vascular puncture relative to the skin surface, may be able to withdraw the distal end of the vascular closure device a predetermined distance that positions the distal end within the first sealant.

Referring now to FIGS. 1-5B, an example vascular treatment assembly 2 is shown including a vascular closure assembly 10 and a skin securement device 12. The vascular closure assembly 10 includes a procedural sheath 14, a delivery tube 16, a sealant manifold 18, and a balloon location assembly 20. The vascular closure assembly 10 extends through the skin securement device 12. The procedural sheath 14 provides an interface between the vascular closure assembly 10 and the skin securement device 12. Operating the skin securement device 12 fixes an axial position of the procedural sheath 14 relative to the skin securement device 12, in at least some arrangements, the remaining portions of the vascular closure assembly 10 (e.g., all but the procedural sheath 14) may be able to move axially relative to the skin securement device 12 while the procedural sheath 14 is fixed in a given axial position.

Figure 3A:
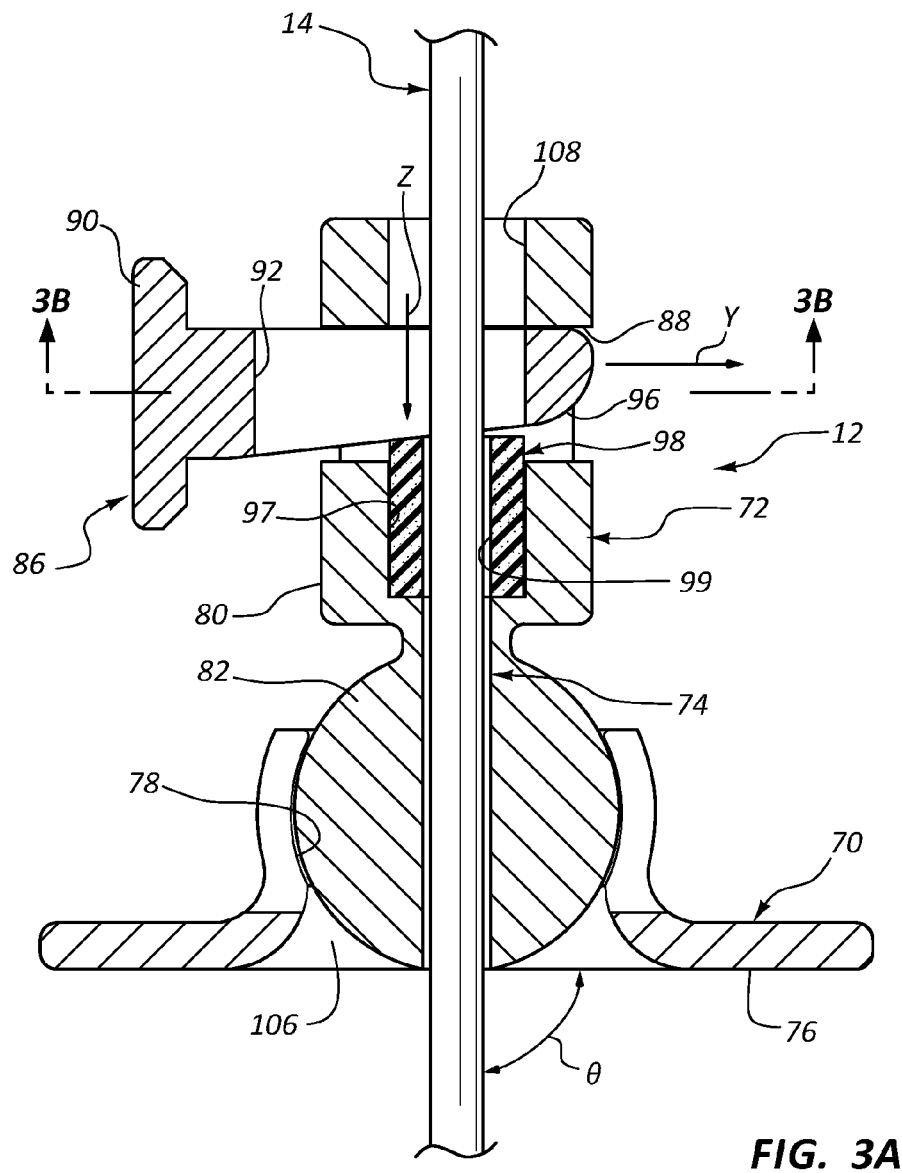
FIG. 3A is a cross-sectional side view of the skin securement device shown in FIG. 1.

The skin securement device 12 may include a base member 70, a securement portion 72, and a sheath passage 74 (see FIG. 3A). In at least some arrangements, the base member 70 may pivot relative to the securement portion 72. This relative pivotal movement between the base member 70 and securement portion 72 may help orient the vascular closure assembly 10 at an angle within a range of angles relative to a skin surface of the patient. An insertion angle of the vascular closure assembly 10 provided by the pivotal movement between the base member 70 and securement portion 72 may substantially match an angle of a tissue tract and vessel puncture through which the vascular closure assembly 10 is advanced.

The skin securement device 12 may include a ball-and-socket arrangement between the base member 70 and securement portion 72. Other arrangements and constructions are possible that provide the desired insertion angle for the vascular closure assembly 10. A ball-and-socket arrangement may provide pivotal movement through an infinite number of angles and planes. Other types of pivot connections may provide pivoting within a single plane or a limited number of plans and rotation angles. In still other arrangements, the securement portion 72 is attached to the base member 70 at a fixed angle orientation having a non-perpendicular angle that represents a common insertion angle, which is typically in the range from about 30° to about 60° relative to the skin surface.

The procedural sheath 14 may include proximal and distal ends 22, 24, and a proximal hub 26 (see FIG. 2). The distal end 24 is typically sized and configured to extend through the skin securement device 12 and into a vessel through a vascular puncture. The proximal end 22 typically includes a proximal opening sized to receive the delivery tube 16. Typically, the procedural sheath 14 has a length sufficient to permit some axial movement of the skin securement device 12 along its length while the procedural sheath 14 is inserted through a vascular puncture during a procedure.

Figures 2A, 2B:
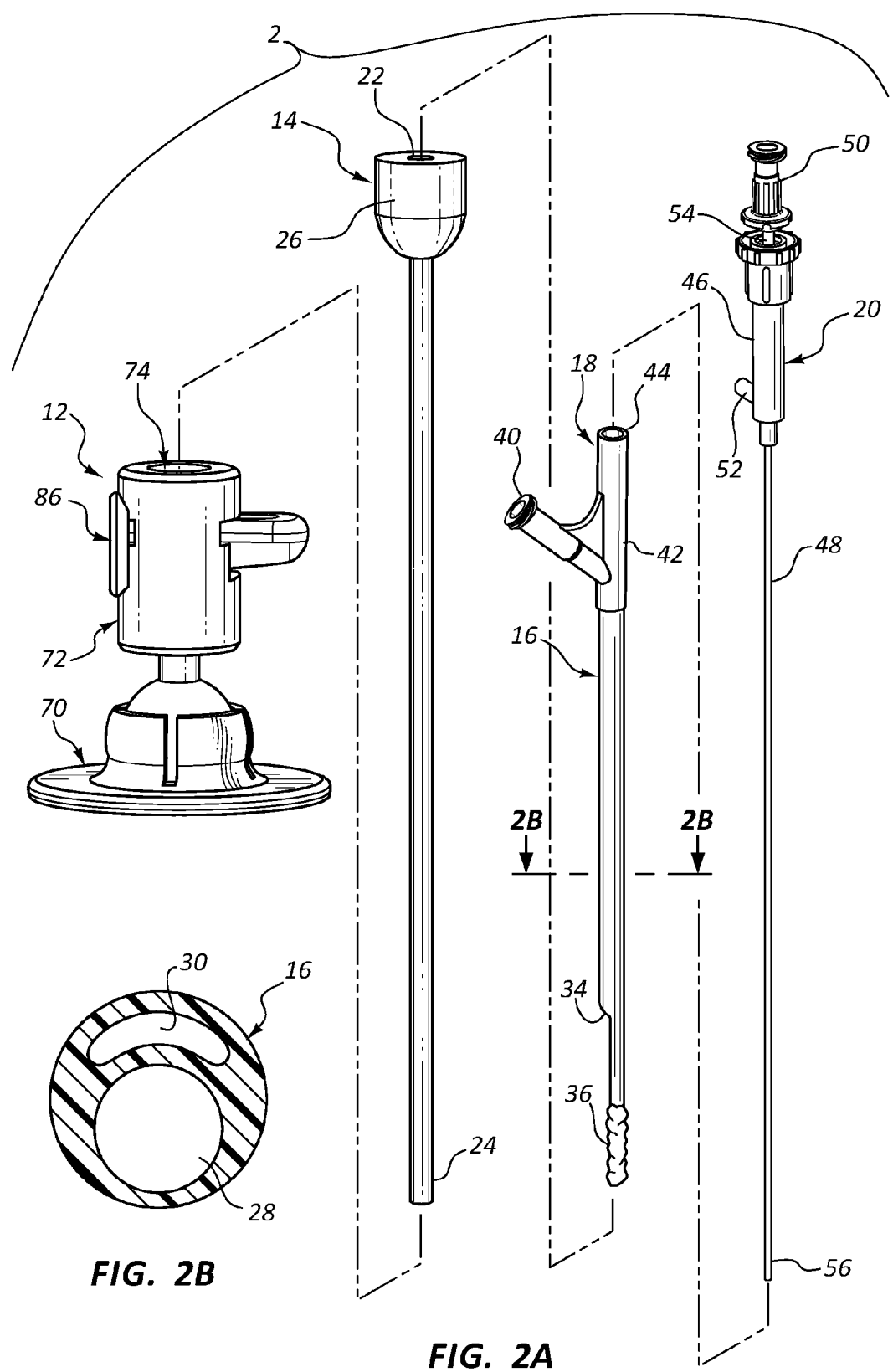
FIG. 2A is an exploded perspective view of the assembly of FIG. 1.
FIG. 2B is a cross-sectional view of a delivery tube shown in FIG. 2A taken along cross-section indicators 2A-2A.

The delivery tube 16 may be configured as a dual lumen tube having a first lumen 28 and a second lumen 30 (see FIG. 2B). The first lumen 28 may be in fluid communication with a balloon 36 positioned at a distal end of the delivery tube 16. The second lumen 30 may have a distal opening 34 that is positioned at a distal end of the delivery tube 16 and proximal of the balloon 36. The first lumen 28 may be connected in fluid communication with a source of inflation fluid as discussed further below. The second lumen 30 may be connected in fluid communication with a volume of bioadhesive sealant used to seal the vascular puncture.

The sealant manifold 18 may include an injection port 40, a distal end 42, and a proximal end 44. The injection port 40 is typically coupled in fluid communication with the second lumen 30. The delivery tube 16 is inserted into the distal end 42. The balloon location assembly 20 is inserted into the sealant manifold 18 at the proximal end 44.

In other arrangements, the vascular closure assembly 10 is void of the sealant manifold 18, and the delivery tube 16 comprises a single lumen. The sealant, inflation fluid, and other features of the vascular closure assembly 10 needed for treatment of a vascular puncture may be delivered through a single lumen in other arrangements, the deliver tube 16 may have more than two lumens and the sealant manifold 118 may include more than one injection port.

An example sealant manifold for use in the vascular closure assembly 10 is described in U.S. Application No. 61/589,930 filed on 24 Jan. 2012 and entitled "Bioadhesive Delivery Catheter Manifold with Mixing Fixture and Methods," which is incorporated herein in its entirety by this reference.

The balloon location assembly 20 may include a housing 46, an inner tube 48, an inner tube manifold 50, and an inflation manifold 52. The inner tube 48 may extend completely through the housing 46 and have a length sufficient to extend through the first lumen 28 of the delivery tube 16 to a position distal of the delivery tube 16. The inner tube manifold 50 may be connected at a proximal end 54 of the inner tube 48. The inner tube manifold 50 may be configured to connect, for example, a source of secondary bioadhesive sealant for use in further sealing the vascular puncture. The distal end 56 of the inner tube 48 may have mounted thereto, for example, a detachable sealing tip. An example detachable sealing tip and associated structure for depositing the sealing tip is described in U.S. Application No. 61/590,027 filed on 24 Jan. 2012 and entitled "Bioresorbable Tip with Low Force Release and Methods," which is incorporated herein in its entirety by this reference.

The inflation manifold 52 may be configured to connect an inflation fluid source to the balloon location assembly 20.

The inflation fluid may travel through the housing 46 and the first lumen 28 of the delivery tube 16 to the balloon 36.

The balloon location assembly 20 may be configured to provide a visual indicator of a size, shape or inflation pressure of the balloon 36. In one example, the housing 46 is substantially transparent and includes a piston therein connected to the inner tube 48. The inner tube 48 may be connected at or near its distal end 56 to the balloon 36 (e.g., to a distal waist of the balloon 36). As the balloon 36 inflates, the inner tube 48 moves axially to move the piston within the housing 46, which movement is visible by the operator and represents a condition of the balloon 36. Details concerning an example balloon location assembly are described in U.S. Application No. 61/590,000 filed on 24 Jan. 2012 and entitled "Balloon Location Device Manifold for Vascular Closure Device and Methods," which is incorporated herein in its entirety by this reference.

While a specific vascular closure assembly is shown and described herein, other types of vascular close assemblies including different types of vascular closure devices, sheaths, sealing materials and other components may be used and may benefit from use with the skin securement devices disclosed herein.

Referring now to FIGS. 3A-5B, the skin securement device 12 is shown in operation with the procedural sheath 14. The base member 70 of the skin securement device may include a skin contact surface 76 and a socket 78. The skin contact surface 76 typically has a perimeter size that is greater than the size of an opening into a percutaneous incision that leads to a vessel puncture. The socket 78 may provide a pivot surface that provides relative rotational and pivotal movement between the base member 70 and the securement portion 72.

The securement portion 72 may include a housing 80, a ball feature 82 that interfaces with the socket 78, a securing assembly 86, and a securing cavity 88. The securing cavity 88 may be formed in the housing 80 in a direction substantially perpendicular to the sheath passage 74. At least portions of the securing assembly 86 may extend through the securing cavity 88. The securing cavity 88 may intersect with the sheath passage 74 (see FIG. 3B).

The sheath passage 74 includes a first passage portion 106 defined in the base member 70, and a second passage portion 108 defined in the securement portion 72. The first passage portion 106 may have a greater diameter than the second passage portion 108 to permit an increased range of pivotal motion between the base member 70 and securement portion 72.

The ball 82 may be snap-fit into the socket 78 to provide a releasable connection between the base member 70 and securement portion 72. In other arrangements, the base member 70 may include multiple parts, which when disassembled permit removal of the ball 82 from the socket 78, and when assembled fix the ball 82 within the socket 78.

Figure 4A:
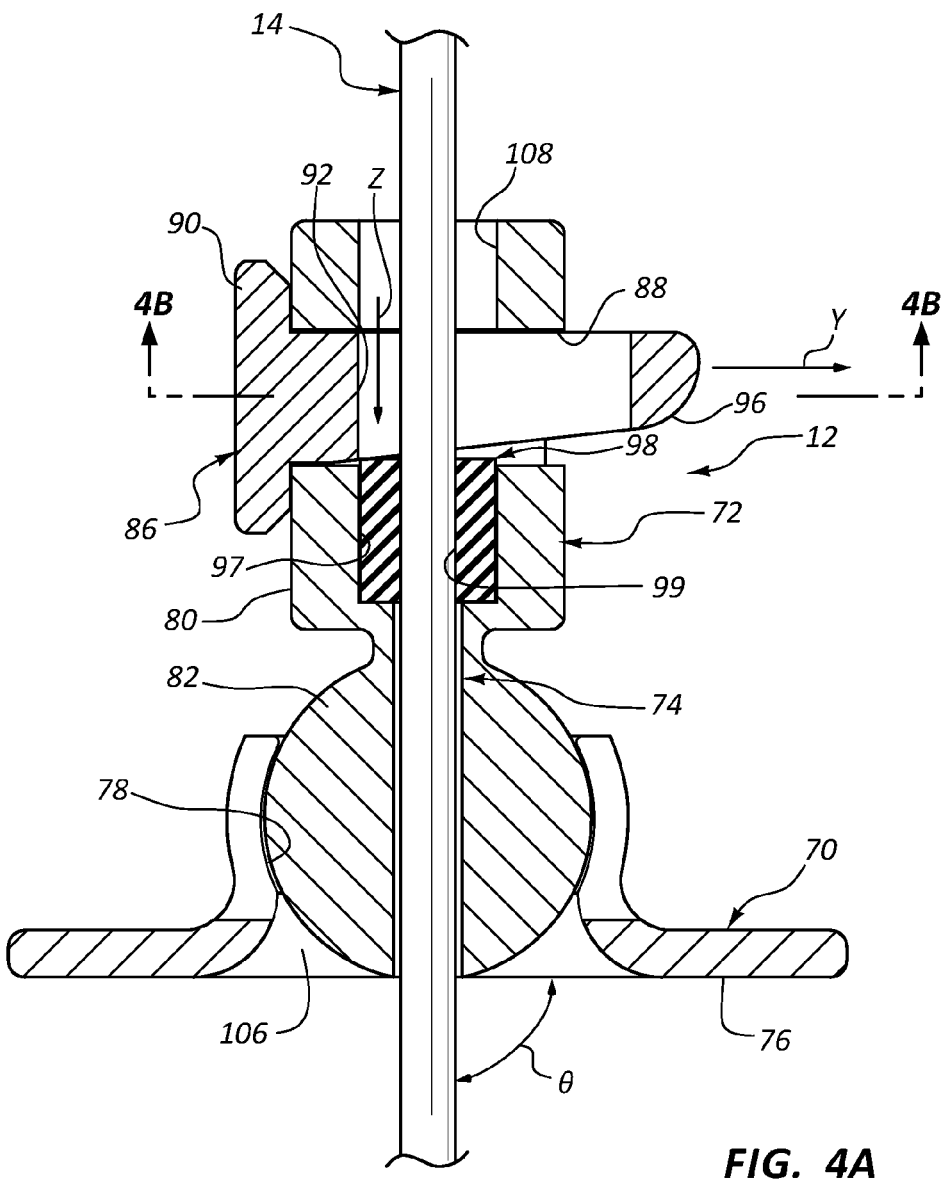
FIG. 4A is another cross-sectional view of the skin securement device of FIG. 1 in an actuated position.

The securing assembly 86 may include an actuator portion 90, a sheath slot 92, a compression surface 96, and a restricting member 98 having a restricting passage 99. The actuator portion 90 may move in a lateral Y direction (see FIG. 3A). The compression surface 96 may have a tapered construction so that advancing the actuator portion 90 in the Y direction applies a force in an axial Z direction to the restricting member 98. The force applied in the Z direction compresses the restricting member 98 within a restricting member cavity 97 of the housing 80, as shown in FIG. 4A. As the restricting member 98 is compressed, the restricting passage 99 reduces in diameter and contacts an outer surface of the procedural sheath 14 to apply a radially constricting force on the procedural sheath 14. The lateral movement of the actuator portion 90 applies an axial force in the Z direction to the restricting member 98 that in turn applies a radially inward directed constricting force on the procedural sheath 14 that fixes an axial position if the procedural sheath 14 relative to the skin securement device 12.

In some arrangements, the actuator portion 90 is biased in a Y direction that applies the constricting force on the procedural sheath 14. The actuator portion is actuated against the biasing force to release the securing assembly 86 from the procedural sheath 14. An example of an actuator portion 90 that may be biased into the closed or constricted position is shown and described with reference to FIG. 6A-7B below.

Figure 3B:
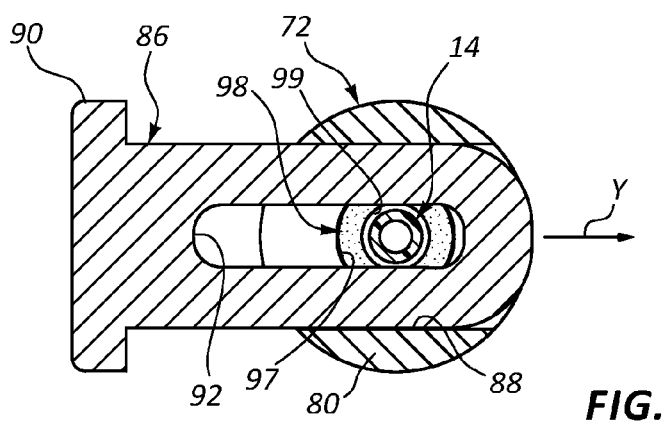
FIG. 3B is a cross-sectional view of the skin securement device of FIG. 3A taken along cross-section indicators 3B-3B.
Figure 4B:
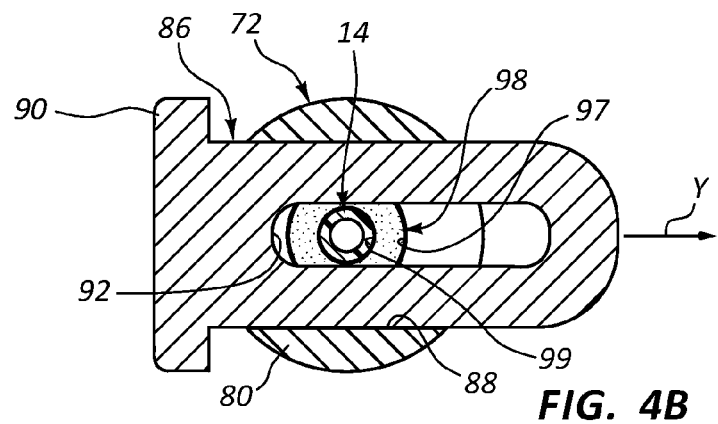
FIG. 4B is a cross-sectional view of the skin securement device of FIG. 4A taken along cross-section indicators 4B-4B.

FIGS. 3B and 4B illustrate how the procedural sheath 14 moves within the sheath slot 92 as actuator portion 90 moves in the lateral Y direction. The procedural sheath 14 may be free floating and move unrestricted within the sheath slot 92.

Figure 5:
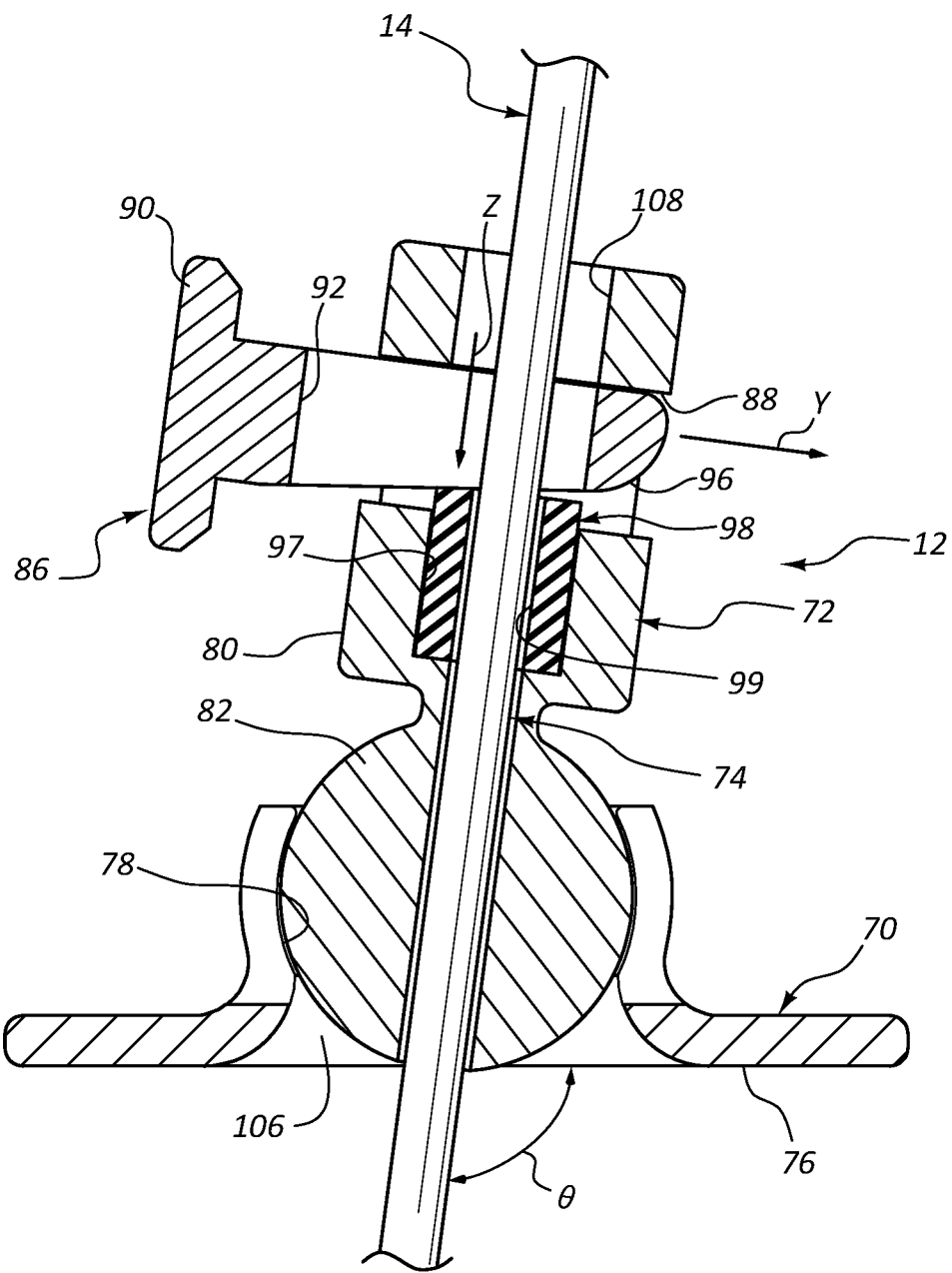
FIG. 5 is a cross-sectional view of the skin securement device of FIG. 1 in a pivoted position.

Referring to FIG. 5, the securement portion 72 is shown pivoted into an angle θ greater than 90°. Typically, the angle θ is in the range from about 90° to about 160°, and more preferably in the range from about 120° to about 150°.

Referring now to FIGS. 6A-7B, another example skin securement device 112 as shown and described in operation with the procedural sheath 14. This skin securement device 112 includes a base member 170, a securement portion 172, and a sheath passage 174. The base member 170 includes a skin contact surface 176 and a socket 178. The securement portion 172 includes a housing 180, a ball 182 that interfaces with the socket 178, a securing assembly 186, and a securing cavity 188. The sheath passage 174 includes a first passage portion 206 defined in a base member 170, and a second passage portion 208 defined in the securement portion 172.

The securing assembly 186 provides a different structure for applying a force to the procedural sheath 14 to fix an axial position of the procedural sheath 14. The securing assembly 186 includes an actuator portion 190, a stop portion 191, a sheath slot 192 and a biasing member 194. The biasing member 194 biases the actuator portion 190 in a lateral direction Y that fixes the axial position of the procedural sheath 14. The sheath slot 192 includes a contact portion 193 and an open portion 195. The procedural sheath 14, when positioned within the open portion 195, is able to freely move axially relative to the skin securement device 112. When the procedural sheath 14 is positioned within the contact portion 193 of the sheath slot 192, the procedural sheath 14 is forced against a sidewall of the sheath passage 174 and wedged within the sheath slot 192 thereby restricting an axial position of the procedural sheath 14 relative to the skin securement device 112.

Figure 6A:
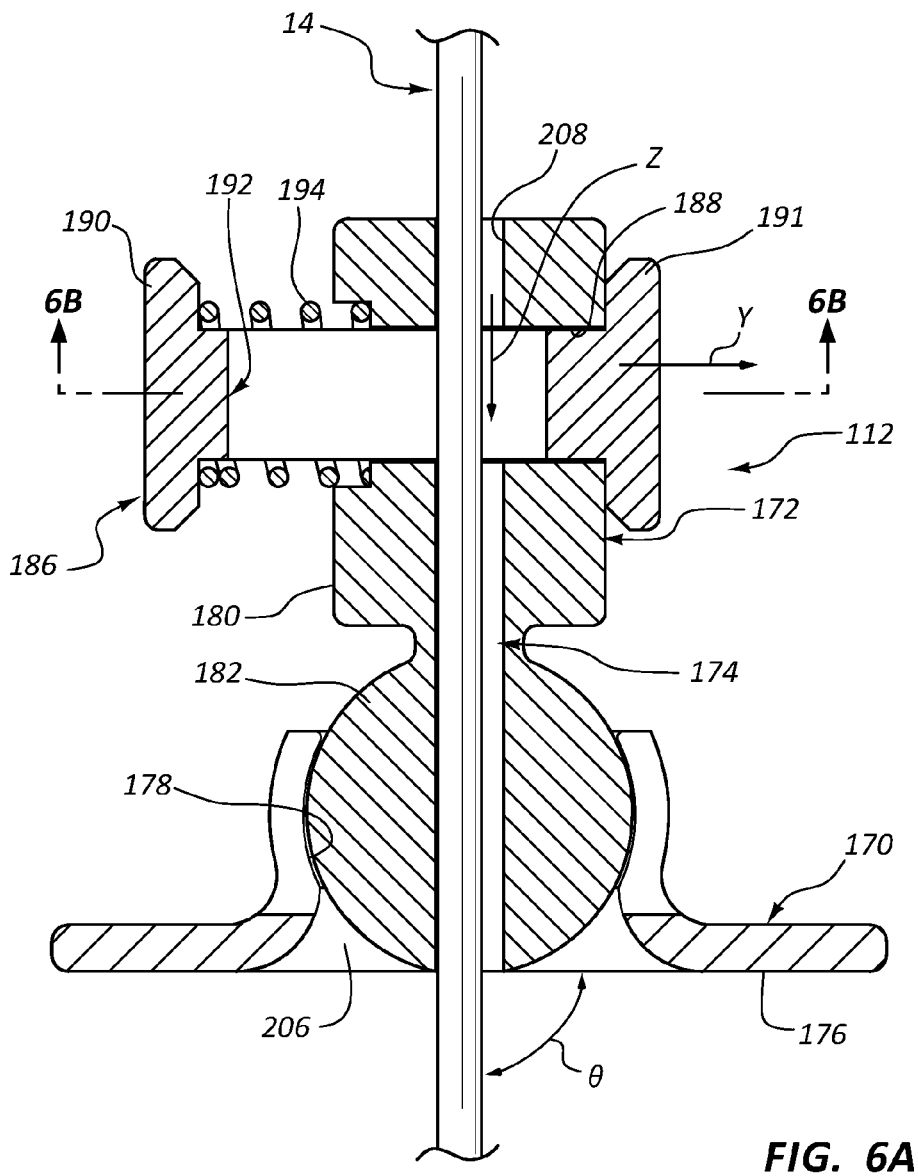
FIG. 6A is a cross-sectional view of another example skin securement device in accordance with the present disclosure.
Figure 6B:
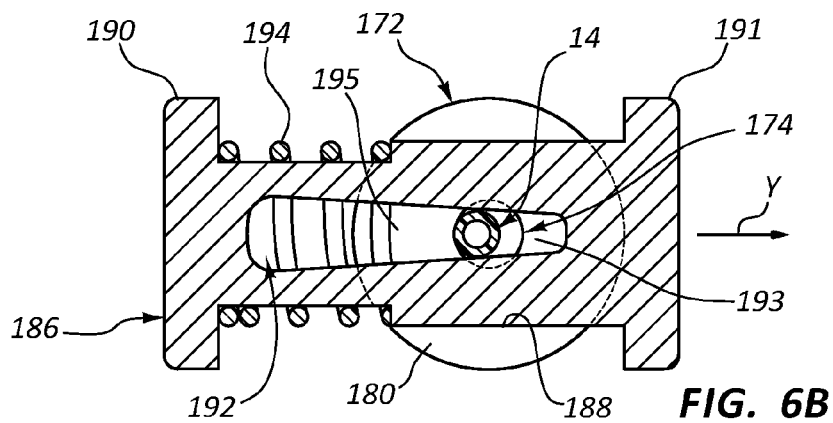
FIG. 6B is a cross-sectional view of the skin securement device of FIG. 6A taken along cross-section indicators 6B-6B.

FIG. 6B shows the procedural sheath 14 in a locked or fixed position in which the procedural sheath 14 is wedged within the contact portion 193 of the sheath slot 192. FIG. 7B shows the procedural sheath 14 positioned within the open portion 195 of the sheath slot 192 to provide free axial movement of the procedural sheath 14 relative to the skin securement device 112.

The biasing member 194 is shown in FIGS. 6A-7B biasing the actuator portion 190 into a close or locked position. In other embodiments, the opposite arrangement may be provided in which the biasing member 194 operates on an opposite side in contact with the stop portion 191 to bias the actuator portion into an open or unlocked position. The arrangement shown in FIGS. 6A-7B may have certain advantages for the operator. The operator may depress or actuate the actuator portion 190 in the lateral direction Y to slide the skin securement device 112 along the length of the procedural sheath 14 and into contact with an outer skin surface of the patient.

The operator may then release the actuator portion 190, which causes the biasing member 194 to move the actuator portion 190 into contact with the procedural sheath 14 to lock the axial position of the procedural sheath 14 relative to the skin securement device 112. The operator then has both hands available for operating the vascular closure assembly 10 to treat the patient while the skin securement device 112 operates to hold the procedural sheath 14 in a fixed axial position. In some situations, the operator may apply a distally-directed axial force on the skirt securement device 112 or a procedural sheath 14 to maintain contact of the skin securement device 112 with the outer skin surface of the patient while operating the vascular closure assembly 10.

Figure 8:
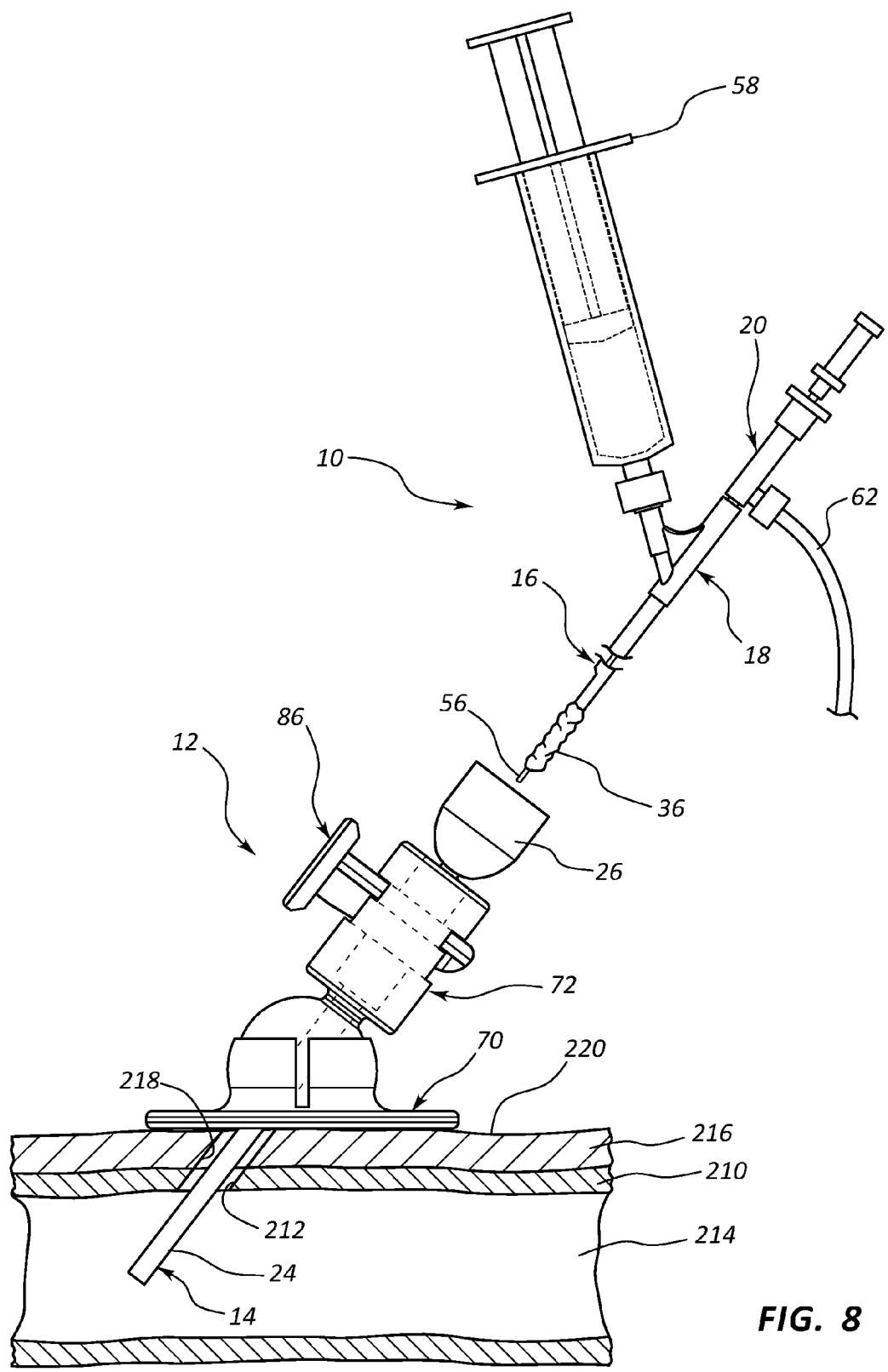
FIGS. 8-13 illustrate operation of the vascular closure assembly and the skin securement device of FIG. 1 to seal a vessel puncture in accordance with the present disclosure.

Referring now to FIGS. 8-13, an example method of sealing a vascular puncture is shown and described with reference to the vascular closure assembly 10 and skin securement device 12. The procedural sheath 14 is advanced through the skin securement device 12 as shown in FIG. 8. The procedural sheath 14 is advanced through a tissue tract 218 of a tissue layer 216, and through a vessel puncture 212 of a vessel 210 and into the vessel lumen 214. Initially, the skin securement device 12 may be positioned out of contact with a skin surface 220. The balloon location assembly 20 is advanced through the sealant manifold 18 and delivery tube 16, and the delivery tube 16 is prepared for insertion into the procedural sheath 14.

Figure 9:
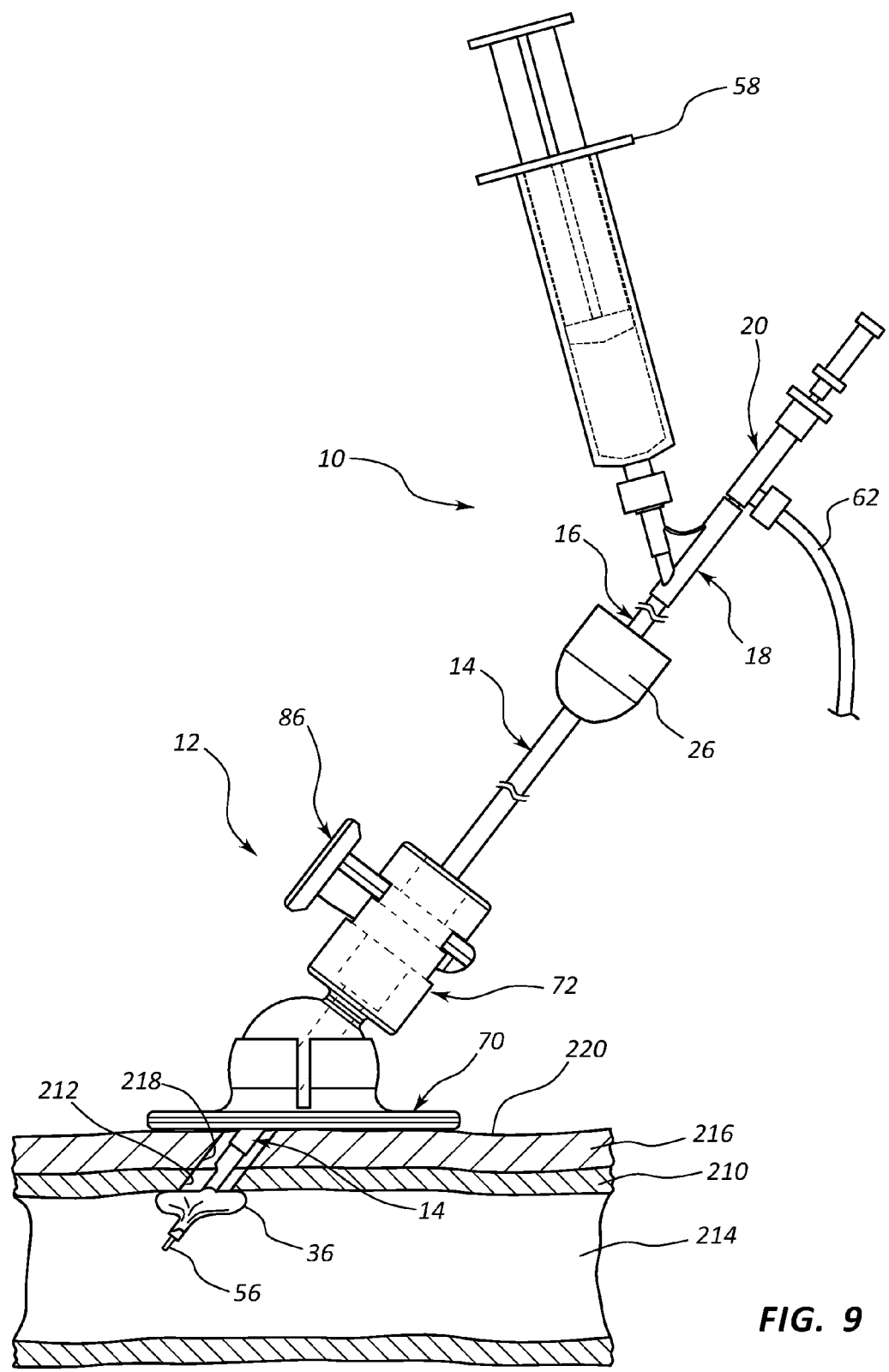

FIG. 9 illustrates the delivery tube 16 and balloon location assembly 20 advanced through the procedural sheath 14 to position the balloon 36 within the vessel lumen 214. A volume of inflation fluid is delivered from an inflation fluid source 62 and through the balloon location assembly 20 and first lumen 28 of the delivery tube 16 to inflate the balloon 36. The vascular closure assembly 10 and skin securement device 12 are withdrawn proximally to bring the inflated balloon 36 into contact with an inner surface of the vessel 210 to temporarily seal the vessel puncture 212 from within the vessel 210. In some arrangements, the skin securement device 12 may remain out of contact with the outer skin surface 220 during inflation of balloon 36 and locating the vessel puncture 212.

Figure 10:
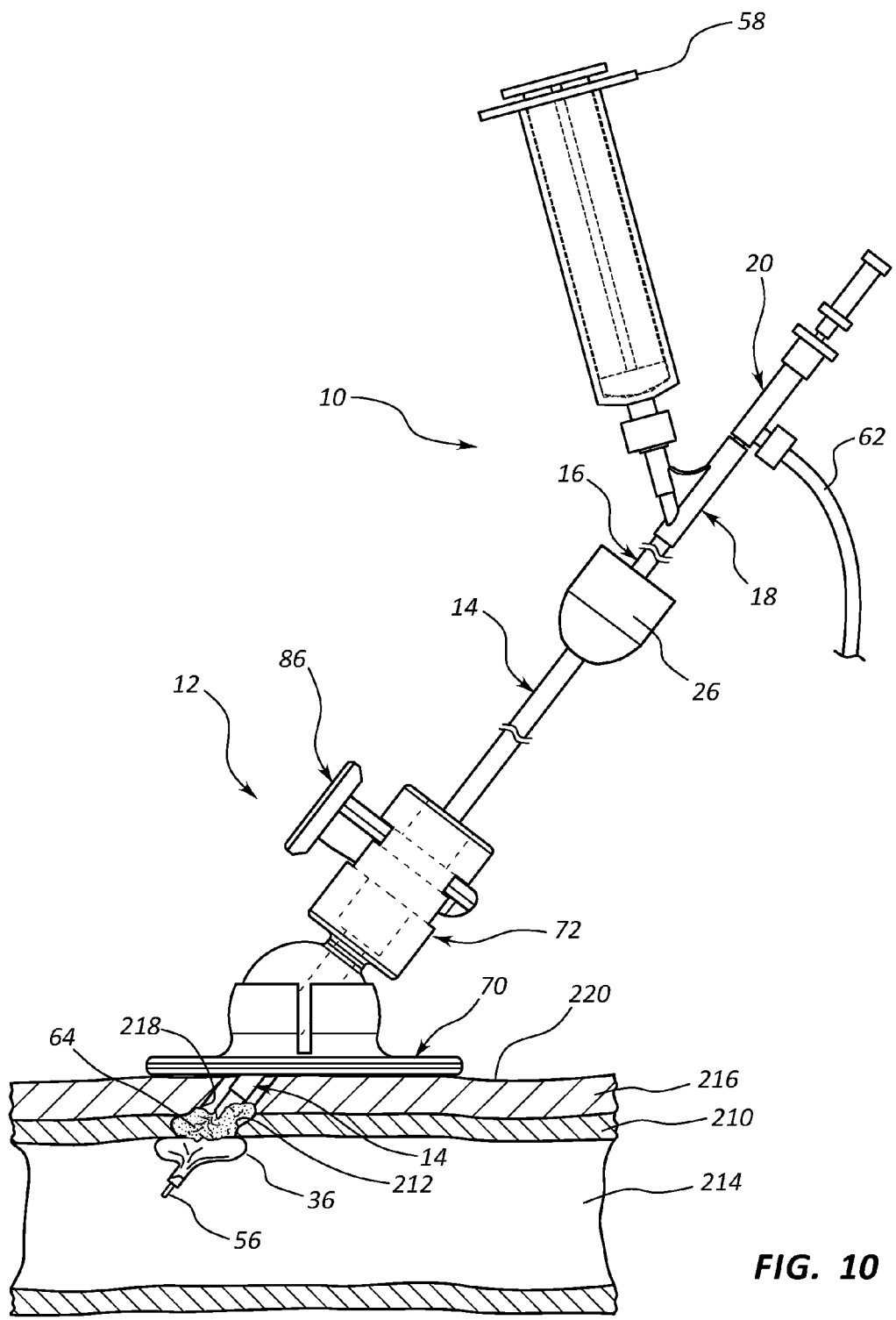

Referring to FIG. 10, a volume of bioadhesive sealant is delivered from a first bioadhesive carrier 58, through the sealant manifold 18 and second lumen 30 of the delivery tube 16, and out of the distal opening 34 to a location outside of the vessel 210 and adjacent to the vessel puncture 212. The bioadhesive material may form a first bioadhesive plug 64 that seals closed the vessel puncture 212 and at least partially seals closed the tissue tract 218 from outside of the vessel 210. The balloon 36 remains inflated and in contact with an inner surface of the vessel 210 during delivery of the first bioadhesive plug 64 to help limit passage of the first bioadhesive plug 64 into the vessel lumen 214. In at least some methods, the first bioadhesive plug 64 is allowed to cure for a predetermined amount of time in which the first bioadhesive plug 64 obtains a solid or semi-solid state.

Figure 11:
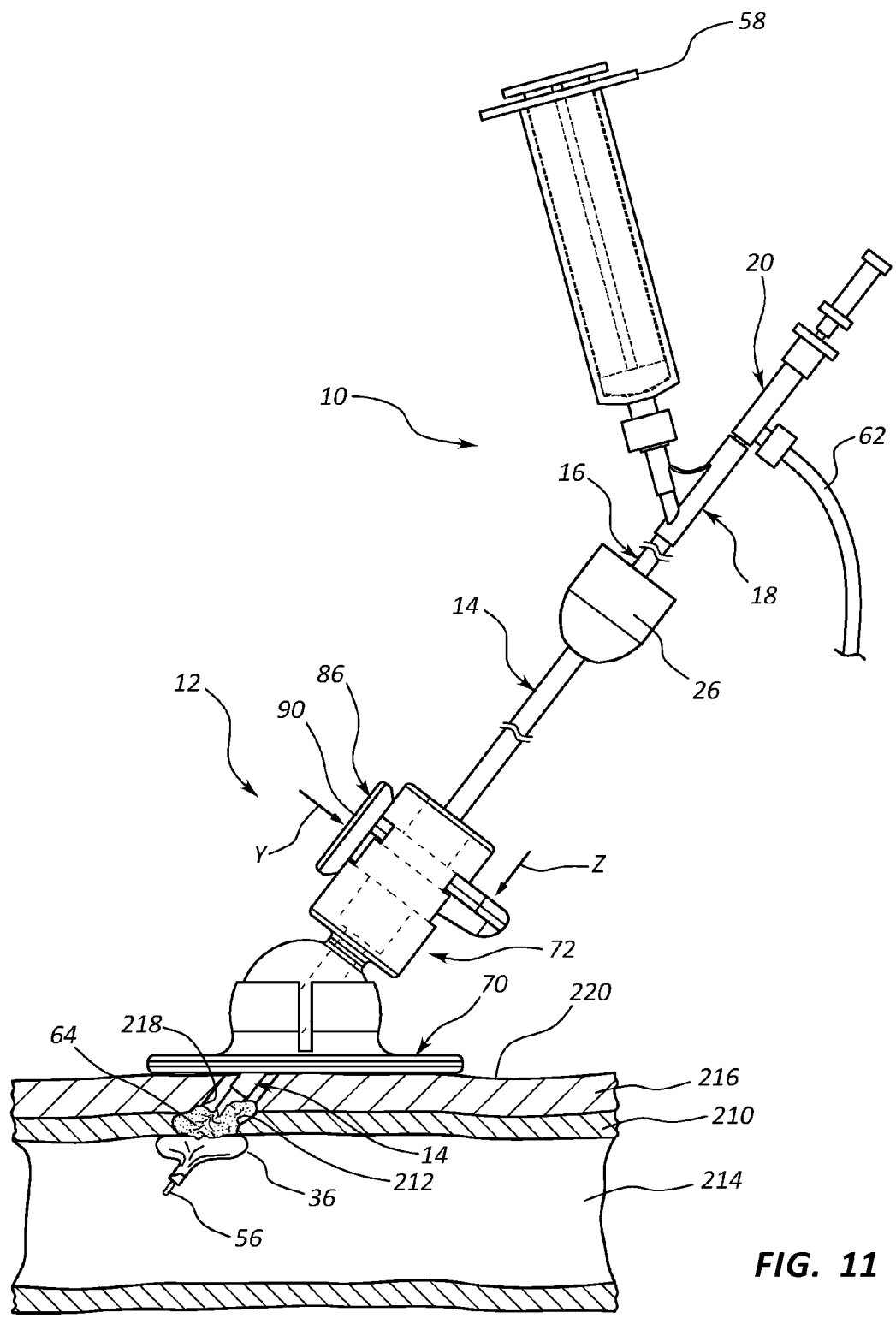

Referring now to FIG. 10, the skin securement device 12 is positioned in contact with the outer skin surface 220 (e.g., advanced along the procedural sheath 14) prior to deflating the balloon 36 and removing the balloon 36 from contact with the inner surface of the vessel 210. In some arrangements, the skin securement device 12 is positioned in contact with the outer skin surface 220 during delivery of the volume of bioadhesive sealant to the vessel puncture 212 so that no further axial movement of the skin securement device 12 along the procedural sheath 14 is required. The securing assembly 86 is operated to fix an axial position of the skin securement device 12 relative to the procedural sheath 14 as shown in FIG. 11. The distal end 24 of the procedural sheath 14 is fixed axially relative to the tissue tract 218 and vessel puncture 212. In other arrangements, the skin securement device 12 may be positioned in contact with the outer skin surface 220 at any time during the procedure. The securing assembly 86 is preferably operated to fix the axial position of the procedural sheath 14 while the balloon 36 is in contact with the internal surface of the vessel 210 so that the procedural sheath 14 may provide a position reference in the axial direction for future axial movement of the delivery tube 16 relative to the procedural sheath 14.

Figure 12:
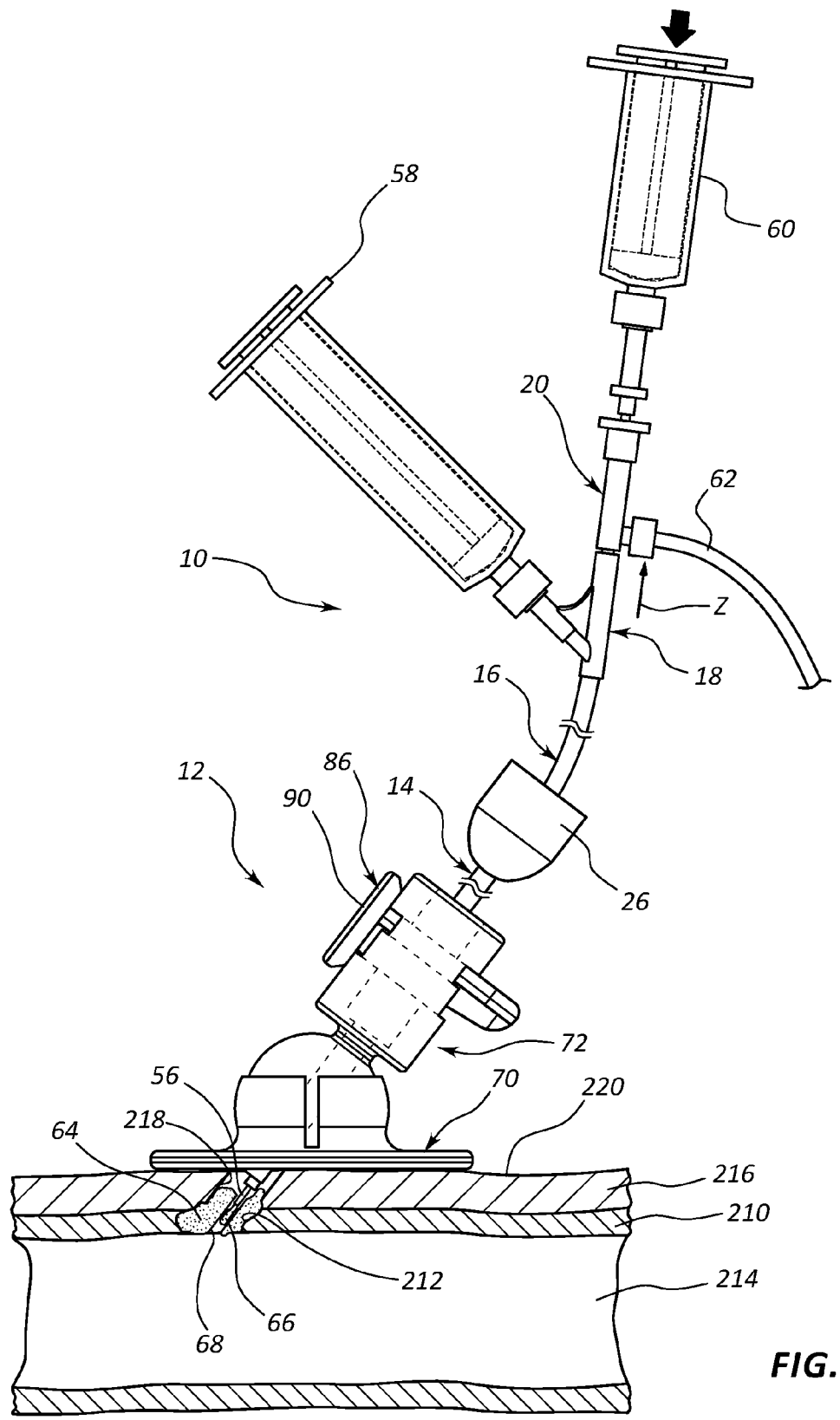
Figure 13:
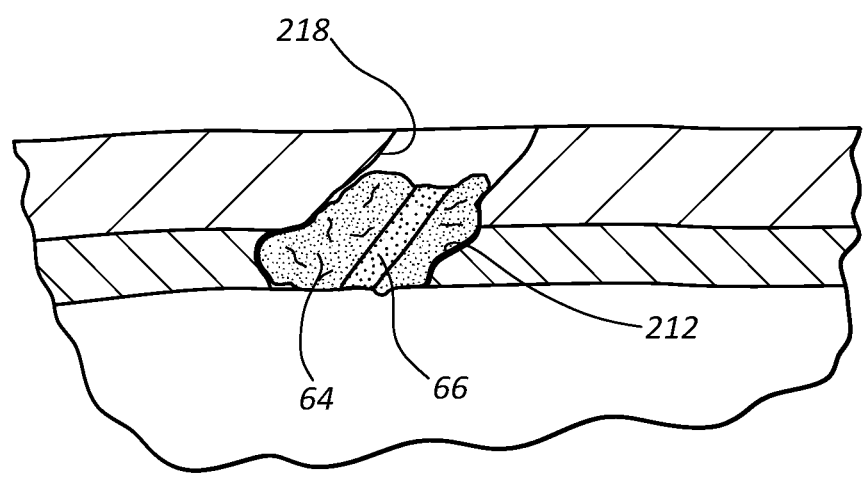

Referring to FIG. 12, the balloon 36 is deflated and the delivery tube 16, sealant manifold 18 and balloon location assembly 20 are withdrawn a predetermined distance to position the distal end 56 of the inner tube 48 within a tract 68 defined in the first bioadhesive plug 64. The predetermined distance may be visually tracked along a length of the delivery tube 16 that is exposed proximally beyond a proximal end of the procedural sheath 14. In one example, the delivery tube 16 includes a plurality of markings or indicia along its nuclear surface that show progress of relative axial movement between the procedural sheath 14 and the delivery tube 16.

The tract 68 may be defined upon removal of the delivery tube 16 through the first bioadhesive plug 64. The balloon location assembly 20 is operated to seal the tract 68. In one example, a secondary bioadhesive material is provided by a second bioadhesive carrier 60 and delivered through the inner tube 48 to the tract 68 to form a second bioadhesive plug 66 (see FIG. 13). In another example, a sealing tip carried at the distal end 56 of the inner tube 48 is released within the tract 68 to seal the tract 68.

In one example, a suture is delivered through the inner tube 48 and is used to detach a detachable sealing tip within the tract 68. The suture may extend primarily out of the inner tube manifold 50 and may be used in combination with or in place of a volume of secondary bioadhesive material supplied by the second bioadhesive carrier 60.

The bioadhesive materials discussed herein may comprise a single component, or may comprise multiple sealant components that are mixed together. The multiple sealant components may further react together to form a crosslinked network. The sealant components may be naturally derived or synthetic. Some example synthetic components include polyethers such as polyethylene glycol, polypropylene glycol and polytetrahydrofuran. Other examples of synthetic components may include polyamine compositions such as polyvinylpyrrolidones, polyethylene imines and hydrogenated polyacrylonitriles. Other example sealant components include polyacrylic and methacrylic compounds such as polyacrylic acid. Example naturally derived components include protienaceous compositions such as albumin, collagen and polylysine. Other examples include carbohydrate compositions such polyhyaluronic acid. The sealant components may also contain reactive functional groups to promote chemical crosslinking. The sealant components may be cross-linked by any known method including, for example, condensation reactions, Michael addition, and free radical. Functional groups used for cross-linking may include, for example, thiols, acrylates, amines, succinimydyls and aldehydes, to name a few.

The preceding description has been presented only to illustrate and describe exemplary embodiments of the invention. It is not intended to be exhaustive or to limit the invention to any precise form disclosed. Many modifications and variations are possible in light of the above teaching. It is intended that the scope of the invention be defined by the following claims.

What is claimed is:

1. A procedural sheath holding device, comprising:
a base member positionable in contact with an outer skin surface adjacent to an incision;
a securing member pivotally attached to the base member and having a securing portion and a compressible member, the securing portion being operable to releasably secure a procedural sheath in a fixed axial position relative to the outer skin surface when a vascular closure device is inserted through the procedural sheath to seal the incision, the securing portion being operable to laterally slide within the securing member, wherein lateral movement of the securing portion applies a radially-oriented force against at least two sides of the procedural sheath by compression of the compressible member against the at least two sides of the procedural sheath.

2. The procedural sheath holding device of claim 1, further comprising a passage extending through the base member and securing member and sized to receive the procedural sheath.

3. The procedural sheath holding device of claim 2, wherein the securing member is configured to contact the procedural sheath within the passage.

4. The procedural sheath holding device of claim 2, wherein the securing member is operable laterally to capture the procedural sheath against a fixed wall within the passage.

5. The procedural sheath holding device of claim 1, wherein the securing member is operable to apply a radial compression force on the procedural sheath.

6. A procedural sheath holding member, comprising:
a base member having a first end configured to be in contact with a skin surface adjacent to a tissue puncture;
a pivot member pivotally attached to the base member and spaced from the skin surface by the base member;
a compressible member;
a passage extending through the base member, compressible member, and pivot member, the passage configured for passage of a procedural sheath;
a securing device operable within the passage to fix an axial position of the procedural sheath relative to the skin surface, a portion of the securing device being operable to laterally slide within the securing device, wherein lateral movement of the portion of the securing device compresses the compressible member to apply a radially-oriented force against at least two sides of the procedural sheath.

7. The procedural sheath holding member of claim 6, wherein the securing device is positioned on the pivot member.

8. The procedural sheath holding member of claim 6, wherein the securing device is operable to apply a lateral force to the procedural sheath within the passage.

9. The procedural sheath holding member of claim 6, wherein the securing device includes a securement portion having a slot through which the procedural sheath passes, and actuating the securement portion captures the procedural sheath between a surface of the pivot member and a surface of the securement portion.

10. The procedural sheath holding member of claim 6, wherein the securing device is operable to apply a radially constricting force on the procedural sheath.

11. The procedural sheath holding member of claim 6, wherein the base member includes a socket feature and the pivot member includes a ball member that interfaces with the socket feature.

12. A procedural sheath holding device, comprising:
a base member positionable in contact with an outer skin surface adjacent to an incision;
a securing member pivotally attached to the base member and having a securing portion and a biasing member, the securing portion being operable to releasably secure a procedural sheath in a fixed axial position relative to the outer skin surface when a vascular closure device is inserted through the procedural sheath to seal the incision, the securing portion being operable to laterally slide within the securing member and through the biasing member, wherein lateral movement of the securing portion applies a radially-oriented force against at least two sides of the procedural sheath.

* * * * *